United States Patent [19]

Hapworth et al.

[11] Patent Number: 4,940,585

[45] Date of Patent: Jul. 10, 1990

[54] METHOD FOR THE TREATMENT OF NICOTINE WITHDRAWAL SYNDROME

[76] Inventors: William E. Hapworth; Mada S. Hapworth, both of 250 W. 57th St., New York, N.Y. 10019

[21] Appl. No.: 312,954

[22] Filed: Feb. 17, 1989

[51] Int. Cl.⁵ .......................... A61K 9/20; A61K 9/14; A61K 9/48; A61K 31/135

[52] U.S. Cl. .................................... 424/464; 424/484; 424/489; 514/651; 514/810; 514/813; 514/252

[58] Field of Search ............... 514/651, 810, 813, 252; 424/464, 484, 489

[56] References Cited

U.S. PATENT DOCUMENTS

| | | | |
|---|---|---|---|
| 4,626,549 | 12/1986 | Molloy et al. | 514/651 |
| 4,683,231 | 7/1987 | Glassman | 514/813 |
| 4,683,235 | 7/1987 | Hynes | 514/651 |
| 4,777,173 | 10/1988 | Shrotryia et al. | 514/252 |
| 4,800,204 | 1/1989 | Mueller | 514/813 |

OTHER PUBLICATIONS

Glassman, *JAMA*, 259(19), 2863–2866 (May 20, 1988).
Cox, *JAMA*, 260(11), 1553 (Letters, Sep. 16, 1988).

*Primary Examiner*—Joseph L. Schofer
*Assistant Examiner*—Carmen B. Pili-Curtis
*Attorney, Agent, or Firm*—Lerner, David, Littenberg, Krumholz & Mentlik

[57] ABSTRACT

A therapeutic method for treatment of nicotine withdrawal syndrome symptoms of a patient in need thereof by administering to the patient a therapeutic composition of a pharmaceutically acceptable carrier and fluoxetine in an amount effective to provide physiological relief from the withdrawal symptoms.

20 Claims, No Drawings

METHOD FOR THE TREATMENT OF NICOTINE WITHDRAWAL SYNDROME

BACKGROUND OF THE INVENTION

The present invention relates to a method for creating tobacco addiction and in particular to a method in which symptoms of nicotine withdrawal syndrome are relieved, especially the craving for a tobacco product.

Jan. 1989 marks the 25th anniversary of the Surgeon General's report linking cigarette smoking to cancer, heart disease, respiratory disease and other conditions. Despite such information being available to the public, a report prepared by the Surgeon General to mark the anniversary concluded that cigarette smoking remains the single most important preventable cause of death in the United States.

Benowitz, *N. Eng. J. Med.* Vol. 319, No. 20, pp. 1318–1330 (Nov. 17, 1988) notes that many people who smoke cigarettes would like to quit but cannot because they are addicted to the psychoactive drug that is the dependence-producing constituent of tobacco, nicotine.

Benowitz notes that nicotine may also contribute to the diseases for which smoking is a risk factor, particularly heart disease. Nicotine is also present in other tobacco products that are smoked or chewed, which are also addictive and associated with heart and lung disease.

Once nicotine enters the bloodstream it has been shown to cross the blood brain barrier and bind to receptors in the brain, resulting in the release of the neurotransmitter serotonin in the central nervous system's neurohumoral pathways. While nicotine's effect on the neurotransmission of serotonin and the receptors of the presynaptic membrane are poorly understood, it is believed that abstinence from tobacco and nicotine results in the reuptake and accumulation of serotonin in these neurohumoral pathways, that when the release of which is not stimulated by nicotine, results in the symptoms of nicotine withdrawal.

According to Benowitz, in about 80% of tobacco users, the cessation of tobacco use results in the development of nicotine withdrawal syndrome, the symptoms of which include restlessness, irritability, anxiety, drowsiness, increasingly frequent wakings from sleep, impatience, confusion, impaired concentration, carbohydrate craving and weight gain, impaired reaction time and a craving for tobacco. While most symptoms peak within 24 to 48 hours after tobacco use is discontinued, and gradually diminish over a two week period, other symptoms, particularly the craving for tobacco persist for months and even years. This craving for tobacco is the overwhelming reason why so many individuals who try to quit smoking fail to succeed.

Pharmacologic therapies are known to help those addicted to nicotine. Receptor antagonists such as mecamylamine have been used that reduce the satisfaction obtained from tobacco use. This therapy has been unsatisfactory because it has a short term effect of increasing tobacco consumption to overcome the receptor antagonism as well as the number of undesirable side-effects.

Non-receptor antagonists have also been used, such as clonidine, that act upon the alpha$_2$ adrenergic receptors of the central nervous system and reduce the intensity of the craving for tobacco and other tobacco withdrawal symptoms. According to Benowitz, in one recent study clonidine treatment for six weeks was found to be more effective than a placebo, but only for women.

Benowitz reports that the most effective pharmacological approach thus far has been nicotine substitution therapy, using nicotine gum, or other nicotine forms, to slowly wean individuals from their addiction to nicotine and craving for tobacco products containing same. The problem with nicotine substitution therapy is that it involves the administration of the psychoactive constituent of tobacco indicated as a contributor to the diseases for which smoking is a risk factor. Nicotine substitution, additionally, must be tapered leading to nicotine withdrawal and subsequent relapse to smoking on a frequent basis. A therapy that relieved nicotine withdrawal symptoms particularly the long term cravings for nicotine, without the hazards associated with the administration of nicotine, would be highly desirable.

SUMMARY OF THE INVENTION

It has now been discovered that relief is provided within 3 hours to 24 hours to those individuals abstaining from tobacco consumption and suffering the symptoms of nicotine withdrawal syndrome, and particularly to those individuals suffering an intense craving for tobacco products, by administering the anti-depressant drug fluoxetine.

While in the past anti-depressants have been used to treat the depression associated with the cessation of tobacco consumption as one symptom of nicotine withdrawal syndrome, anti-depressant therapy has not been shown to relieve other symptoms of nicotine withdrawal, particularly the craving for tobacco products. What is especially unexpected from the method of the present invention is the virtual immediate relief of tobacco product craving and other symptoms of nicotine withdrawal syndrome provided by fluoxetine once it enters the bloodstream, particularly because fluoxetine and most other anti-depressants are not effective in the treatment of depression until blood levels of the drug build up over a period of several weeks.

According to the present invention, a therapeutic method is provided for the treatment of nicotine withdrawal syndrome symptoms of a patient in need thereof in which a therapeutic composition is administered to a patient containing a pharmaceutically acceptable carrier and fluoxetine in an amount effective to provide physiologically effective relief from the nicotine withdrawal syndrome symptoms, which relief is provided upon entry of the fluoxetine into the patient's bloodstream.

While not being bound by any particular theory, fluoxetine is a known serotonin reuptake inhibitor, and it is believed that by preventing the reuptake of serotonin into the central nervous system's neurohumoral pathways, the symptoms of nicotine withdrawal syndrome are relieved, particularly the intense craving for tobacco products.

DETAILED DESCRIPTION OF THE PREFERRED EMBODIMENT

The method of the present invention is useful in the treatment of individuals seeking to discontinue consumption of tobacco products that suffer from symptoms of nicotine withdrawal syndrome. Nicotine is present in all forms of tobacco products, the discontinued consumption of any of which results in the onset of nicotine withdrawal syndrome. The method of the present invention is equally applicable to the treatment of individuals suffering from symptoms of nicotine withdrawal syndrome resulting from the discontinued use of tobacco consumed in any form, including the smoking of cigarette, cigar or pipe tobacco, or the chewing of snuff or chewing tobacco.

According to the present invention, near immediate relief is provided to those individuals suffering from symptoms of nicotine withdrawal syndrome by administering a therapeutic composition of a pharmaceutically acceptable carrier and fluoxetine in an amount sufficient to provide pharmaceutically effective relief from the nicotine withdrawal syndrome symptoms. The relief is effective immediately upon entry of fluoxetine into the bloodstream and is particularly effective in relieving the intense tobacco product cravings associated with nicotine withdrawal syndrome. Fluoxetine is a new anti-depressant used in the treatment of major depressive disorders and is manufactured under the tradename Prozac.

Fluoxetine is also especially effective in relieving the carbohydrate craving associated with nicotine withdrawal syndrome that typically results in weight gain among individuals who discontinue the use of tobacco products. The effectiveness of fluoxetine in reducing carbohydrate craving has been noted by several studies and the drug has been recommended for the treatment of depression caused overeating. While the reversal of changes in the metabolism caused by nicotine make weight gains of 5 to 10 pounds unavoidable among individuals who discontinue tobacco consumption, the administration of fluoxetine has been found to prevent the larger weight gains typically experienced.

The severity of nicotine withdrawal syndrome symptoms will vary among individuals, and will depend in a large part upon the degree of addiction, that is, how heavily a person smoked. Preferably, a history of tobacco use and prior attempts at quitting should be obtained from a patient prior to administration of fluoxetine to determine the ability of the individual to remain nicotine free. The daily dosage of fluoxetine should be that quantity sufficient to relieve tobacco product cravings and other symptoms of nicotine withdrawal syndrome, without causing the patient to experience the known side-effects of the drug. This is generally in a range of about 5 milligrams (mg) to about 40 mg a day, for individuals of body weight between about 110 lbs. and about 210 lbs. Increased dosages should be given to heavier individuals, who would not experience side-effects at higher dosage levels. Such dosage increases can be readily determined by one of ordinary skill in the medical art. The known side-effects vary with individuals and range from drowsiness to sleepiness. Anxiety, nausea, dizziness and headaches are also common. Should side-effects be experienced, the dosage should be scaled back to a level at which relief is provided without side-effects. The above dosage range is sufficiently broad to afford relief to eve the most severely nicotine addicted side-effect prone individuals. The typical daily dosage for an average tobacco user is 20 mg.

The administration of fluoxetine should begin between 24 and 48 hours after the use of tobacco has been discontinued. The drug is preferably administered in a single dosage in the morning, preferably between 6:00 a.m. and 9:00 a.m., for maximum benefit in reducing cigarette craving and to avoid any insomnia side effect. Because any side-effects usually disappear after the first couple of days, the initial dosage should be maintained for one week before a reduction is considered. Quantities of the daily dosage may also be administered over the course of the day in regular intervals, preferably in two or three doses.

According to the method of the present invention, the therapeutic composition containing fluoxetine may be administered orally in the form of tablets, capsules, dragees, granules or pills. It is contemplated that the therapeutic composition may also be administered by other means, such as by injection, or by infusion with skin patch. The therapeutic composition of fluoxetine with a pharmaceutically acceptable carrier will conform to pharmacologically accepted formulations using conventional materials and ingredients that will vary according to the form of administration. In preparing the desired pharmaceutical form of the therapeutic composition, various additives and diluents can be utilized as carriers, such as starches, gelatin, sugars such as lactose, glycerine, water and polyvinyl alcohol. Tablets are typically prepared with a binder carrier of sugar, starch, gelatin or mixtures thereof. Skin patches are typically prepared with a gel carrier of glycerine, water, polyvinyl alcohol or mixtures thereof.

One or more therapeutic agents capable of relieving symptoms of nicotine withdrawal may be administered in conjunction with fluoxetine. Such therapeutic agents include minor tranquilizers such as benzodiazepines, major tranquilizers and other anti-depressants, or the drugs xanax and buspirone. The therapeutic agents may be included in the therapeutic composition or administered separately.

Relief from symptoms of nicotine withdrawal syndrome, especially the craving for tobacco, results almost immediately upon entry of fluoxetine into the bloodstream. Maximum relief occurs no later that twenty-four hours after the therapeutic composition is administered, ordinarily within twelve hours and usually within two to three hours.

Treatment of nicotine withdrawal syndrome with fluoxetine should continue for approximately one year, over which time the levels of serotonin in the central nervous system's neurohumoral pathways will gradually reach a non-stimulated equilibrium. Over this time the dosage levels of fluoxetine may gradually be reduced. Preferably, the dosage reduction should not begin until the drug has been administered for six months. As the fluoxetine dosage is being reduced, should symptoms of nicotine withdrawal syndrome reappear, the dosage should be increased to a level at which the symptoms are relieved.

The method of the present invention is preferably administered in connection with and/or subsequent to an educational and/or behavioral modification program to ensure continued abstinence from tobacco products once the nicotine addiction is conquered. The method of the present invention is also highly beneficial to these programs by eliminating the suffering experienced from the nicotine withdrawal syndrome over the course of these programs, which not only allows the programs to focus on their educational or behavioral modification goals, but also reduces the incidence of program non-completion.

The following examples serve to provide further appreciation of the invention, but are not meant in any way to restrict the effective scope of the invention.

EXAMPLES

A group of five females and five males participated in a stop-smoking program in which fluoxetine was administered in its commercially-available form, Prozac. The ages of group members ranged between 25 and 52. Prior to entering the program members of the group smoked over a pack of cigarettes a day, many up to two to three packs a day. The combined smoking history of the group was over 585 pack-years. Each group member has tried without success on more than one occasion to stop smoking using methodologies such as acupuncture, nicotine substitution, hypnosis and conventional behavioral modification but were deterred by post-cessation tobacco craving and other symptoms of nicotine withdrawal. Each of these patients on the present regimen were taken to a point of increased smoking and abrupt termination with close monitoring of symptomatology. The general pattern of their withdrawal symptoms represented moderate to severe symptoms which became increasingly severe with an inability to refrain from cigarettes and a feeling of intense desire to smoke. These patients were begun on medication, 20 milligrams of fluoxetine a day, as far away from their cessation point as possible with the purpose of attempting to keep them medication free for 4 to 5 days. Most patients were unable to tolerate more than 2 or 3 days of withdrawal and medication was begun on the average after 2 days. All ten patients experienced near complete remission from symptoms of withdrawal and a profound decrease in cravings for cigarettes. The 20 milligrams of fluoxetine had a rapid response which occurred typically within 2 to 3 hours and a complete response within 24 hours. These patients demonstrates remarkable improvement on fluoxetine with a subsequent ability to control the severe urges through psychological and behavioral techniques.

EXAMPLE 1

Patient 1 is a 44 year old white female who has been smoking since the age of 11 years old approximately 2 packs per day. This is a 66 pack-year history of smoking which has been interrupted on 4 different occasions in attempts to stop smoking. Patient 1 has tried to utilize 4 different techniques for smoking cessation. Her first attempt was hypnosis which was conducted over a several week period and culminated in continued smoking. The second attempt was a behavioral program which focused on behavioral techniques and helped her stop smoking for a 3 month period. She gained 20 pounds during this cessation and felt extremely depressed, anxious, had severe cravings throughout the period of cessation and was extremely irritable. The patient had severe carbohydrate cravings and ate candy bars on a constant basis. The patient eventually went back to smoking due to nicotine withdrawal symptoms. Her other 2 attempts were with nicotine chewing gum and clonidine which were unsuccessful and produced intolerable side effects.

Patient 1 has a family history significant for both parents having been heavy smokers. Her medical surgical history is unremarkable and her substance abuse history as well is unremarkable.

Patient 1 entered the program reasonably motivated to stop smoking but fearing the weight gain and irritability that she had experienced on previous attempts to stop. She picked a stop date and accomplished it. She experienced severe symptoms of irritability, depression, cigarette cravings, and lack of concentration and anxiety. Her symptoms continued for a week's time unabated with a pattern of increasing severity over time. The patient complained that she felt she would start to smoke and was begun on the medication. The patient experienced a complete reversal of her symptoms of withdrawal within 3 hours of the first dosage of fluoxetine. She stated that she felt normal again with unbelievable lifting of her suffering from nicotine withdrawal and cravings for cigarettes. The patient continued on 20 milligrams per day of fluoxetine experiencing initial nausea and headaches. These symptoms disappeared but insomnia remained as a persistent side affect. The patient was decreased to 10 milligrams per day of fluoxetine and this helped with the insomnia. This patient demonstrated a rapid one to two hour response to fluoxetine and experienced a total alleviation of nicotine withdrawal syndrome and an 80 to 90% decrease in her urges for cigarettes. This patient was noncompliant with medications which illustrated facts about the medication. This patient would forget her morning dosage and stated that by noon she was experiencing severe urges for cigarettes and because of this realized she had not taken the medication. Immediately after taking her dosage of medication the urges disappeared and she felt substantially better.

The patient gained only five to ten pounds on the medication and has stabilized at this juncture with a withdrawal procedure being initiated after six months without smoking.

EXAMPLE 2

Patient 2 is a 38 year old white female who has been smoking since the age of 13 years old. She smokes 2 packs per day and has a 50 pack-year history on the basis of these calculations. The patient has attempted to stop smoking on one occasion through a tapering method. The patient states that she experienced such severe effects from this attempt that she has not subsequently tried to stop. The patient states that when she tapered she experienced severe anxiety, depression, irritability, and symptoms of carbohydrate cravings with a weight gain of 20 pounds. The patient states that she never fully stopped smoking at this juncture and got down to several cigarettes per day.

The patient gives no significant medical history or psychiatric history and has been in good health for her entire life. The patient drinks socially on a 3 to 4 time a week basis 1 to 2 glasses of wine.

The patient entered the program due to extreme fear of the withdrawal symptoms and the inability to cope with stopping smoking without some program. The patient was given a stop date and was able to stop for only 24 hours without smoking. She was encouraged to stay off cigarettes for several days before the medication would be started but she was unable to comply with this request. The patient stopped smoking 2 packs per day but continued to smoke up to 5 to 10 cigarettes per day during this period. It was decided to have her stop smoking for only 24 hours and biological data was performed at that time. The hours and biological data was performed at that time. The patient was given 20 mg fluoxetine and her response was dramatic. The patient within 1 hour felt entirely different and experienced near total alleviation of her symptoms of anxiety, irritability, restlessness, impatience, food cravings, and thirst which had been previously intolerable. The patient continued on 20 mg a day fluoxetine. This patient was asked to stop smoking during the holidays season and in the midst of a job transition. She was under maximal distress and stress but was able to cease smoking with minimal effort. She reported that when she did not take her medication in the early morning she also had severe cravings by noon. This would remind her to take the medication and she was able to decrease her cravings almost instantaneously after taking the medication.

This patient experienced significant drowsiness on the medication but had gone against recommendations about drinking. She continued to drink 1 or 2 glasses of wine on a 2 or 3 time a week basis and the sedative effects were believed to be concurrent to this drinking. The patient decreased her drinking and drowsiness improved moderately. The weight gain with this patient was 10 pounds but significantly less than her previous attempt to stop smoking which was totally unsuccessful. The patient noted significant decreases in her carbohydrate cravings and was able to better control her appetite on the medication than during the one-week period when she was smoking three to ten cigarettes a day.

EXAMPLE 3

Patient 3 is a 35 year old white male who has been smoking since 16 years old. The patient has smoked 3 packs per day with a history of 3 previous attempts to stop smoking. The patient attempted cold turkey, hypnosis, and a behavioral program which utilized the tapering method of nicotine withdrawal. The longest period the patient gave up smoking was for 6 months and he gained 30 pounds with a history of severe depression and irritability, food cravings, lack of concentration, and constant urges during this period. The patient states that he went cold turkey on 1 occasion and stopped smoking for 1 week with similar side effects. The 3rd attempt to stop smoking was in a program for behavioral treatment which was totally unsuccessful and did not culminate in his stopping smoking.

The patient has a history of being in a car accident which required extensive hospital care with a colostomy and resection of his descending colon. The patient recovered adequately but suffered abdominal trauma due to this accident. The patient spent 20 days in the intensive care unit and made a full recovery. Other than that the patient has been in good medical health most of his life. The patient's substance abuse history is insignificant and his family history is significant for a father who smoked heavily and a mother who had a heart attack at age 45.

This patient stopped smoking with subsequent extreme carbohydrate cravings and irritability, lack of concentration, anxiety, depression as well as some insomnia symptoms. This patient additionally stopped smoking during the holidays and experienced severe urges that lasted all day for the first 2 days. He states that he intended to go back to smoking due to his symptoms and 20 mg a day fluoxetine was started. He had a significant response to the medication which consisted of an initial sense of tranquilization and calm which permitted him to go home and go to sleep for 10 to 12 hours. He awoke the next morning feeling completely different than he had for the first 3 days off of cigarettes. He experienced a significant improvement over his urges and carbohydrate cravings that following morning after having taken the medication the previous day at 3 p.m. His progress continued with daily morning dosages of medication and he was able to remain smoking free despite a death in the family. He has gained less than 10 pounds since stopping and feels better than he ever has while smoking or before smoking.

EXAMPLE 4

Patient 4 is a 35 year old white female who has been smoking since 17 years old, 1 pack per day which calculates to be an 18 pack-year history. The patient has given up smoking on 1 previous occasion where she went cold turkey. She states that she had severe urges, extreme food cravings with very prominent anxiety and irritability. The patient states that she quit for only 6 days and returned to smoking due to these symptoms.

The patient's medical history is significant for an ovarian cyst in 1983 but otherwise healthy. The patient has a negative psychiatric history and also has a negative substance abuse history. The patient does drink socially on a several time a week basis up to 2 glasses of wine per occasion. The patient's family history is significant for a mother who smoked heavily and a father who also smoked heavily. The father has had 2 myocardial infarctions. The mother has also had a myocardial infarction and suffers from Diabetes Mellitus.

This patient was someone who minimized her addiction and was unwilling to look at the extent to which she was compelled to smoke. Nonetheless after selecting a stop date she was unable to completely stop smoking with a reduction down to about 10 cigarettes per day. She was still suffering extreme symptoms during this period of carbohydrate craving, insomnia, depression, anxiety, irritability and lack of concentration. She struggled for over a week to stop smoking and was depressed and discouraged at her efforts. The patient was encouraged to stop for 24 hours and biological data was drawn to determine her neurophysiology. The patient was begun on 20 mg a day fluoxetine and experienced a sense of mild to moderate relief within 3 hours of her first ingestion of the medication. The next morning after a 20 milligram dosage of the medication she felt significantly better and less irritable with a better sense of control. This patient additionally experienced sedation on the medication and was unwilling to comply with the restriction of not drinking. She continued to drink on 2 to 3 occasions during the week and her sedation improved only mildly. The patient was encouraged to take the medication at night and this helped with her drowsiness during the day. Despite these side effect of drowsiness the patient experienced relief of her symptoms of withdrawal and a decrease in her urges of significant proportions.

This patient demonstrated extreme denial around her addiction to cigarettes and was unable to fully appreciate the concept of addiction as it related to cigarette smoking. Her physiological data was gathered and she remained cigarette free for five weeks with no urges or symptoms of withdrawal present. The patient experienced job distress and difficulties at work which precipitated a crisis in which she began to smoke again. She also stopped the medication several days prior to this crisis and stopped her contact with us in the treatment. This patient clearly demonstrates the need for an aggressive behavioral educational approach in order for the medication to have its best effect. She readily admits that on the medication she experienced no urges or symptoms of withdrawal but complained about the drowsiness as a probable excuse to stop the medication and start smoking again. Her inability to admit to her addiction to nicotine was crucial in her relapse on cigarettes. The patient has re-entered into the program and we have stressed the educational aspects which were previously not stressed in her case. It is important to recognize that her entrance into the program is directly related to the benefit she experienced on medication and the facility with which she was able to stop smoking.

EXAMPLE 5

Patient 5 is 45 year old white male who has a history of smoking since age 10 years old. He smokes two packs per day with a 70 pack-year history calculated. The patient has tried to stop smoking on 1 previous occasion where he went cold turkey. The patient states he was unable to give up cigarettes for more than several hours with overwhelming urges with anxiety and depression emerging even after 12 hours of not smoking.

The patient is physically obese and weighs approximately 370 pounds. The patient states that he has been overweight his entire life and that his present weight is about his maximum. The patient is unemployed due to his severe obesity and inability to mobilize himself for any other activity other than smoking. The patient's past medical history is essentially negative other than his obesity but he also has a history as a child of having received pituitary injections in order to grow normally. These were stopped at age 16 years old. The patient additionally had hepatitis on a 1 time occasion which was probably related to a past history of IV heroin abuse. The patient's past psychiatric history is significant for a drug rehabilitation in 1986 which resulted in sobriety from heroin. The patient states that he has had significant problems with heroin and other substances of abuse but has been able to maintain himself sober with only periodic smoking of marijuana and 1 or 2 time a year use of methadone. The patient states that this usage is sporadic and relates to not feeling well at the time at which he takes these drugs.

At the time of his entrance into the program the patient has been sober with no drug usage for several months and he presently is motivated to stop smoking. He feels that smoking is a significant deterrent for him to get out and find a job for himself. He states that he has no energy or ability to breathe and participate in any life activities. His psychiatric condition is not significant for depression but he has moderate to severe personality problems. He does not meet criteria for depression and is substance abuse free at present.

The patient has a severe history of smoking but a minimization of his addiction to nicotine. He picked a stop date which he complied with and 3 days after cessation was begun on 20 mg a day fluoxetine. At the time of institution of medication the patient was extremely irritable and anxious with nausea, depression, and symptoms of food cravings being prominent in his clinical picture. He started medication and within 2 hours felt significantly more tranquil with the following morning being a dramatic relief of all symptoms which were objectively noted. He evidently felt better and was able to get up and walk, which had been recommended exercise, for the first time since entering the program and he stated that he felt more in control and capable. It was noted that his moderate cravings for cigarettes disappeared and that his overall attitude and anxiety and irritability symptomatology was insignificantly alleviated.

This patient represents a cross addicted individual who has been able to give up heroin and other substances of abuse but remains severely addicted to nicotine. It is important to recognize that heroin and methadone are considered to be the most severe addictions and this individual was able to give them up but unable to stop his smoking habit.

EXAMPLE 6

Patient 6 is a 30 year old white female who has a history of smoking since age 11 years old. She has smoked 2 packs per day and has attempted to give up cigarettes on 4 different occasions. She has a 38 pack-year history and states that she becomes hot tempered and irritable every time she has tried to stop smoking. The patient has utilized cold turkey, hypnosis, and acupuncture as methods to stop. The longest period she has been able to give up smoking was for one year post acupuncture. The patient states that she smoked marijuana during this period and that this made it easier to not smoke cigarettes. On the other occasions she was able to give up for one month, three months and two weeks. On all occasions the patient experienced severe urges throughout her entire period of not smoking as well as anxiety, depression, irritability, restlessness, impatience and severe weight gain. The patient had marked carbohydrate cravings and states that even during the period when she gave up cigarettes for one year that these symptoms persisted on a moderate basis throughout that entire year. The patient additionally felt that she became dependent on marijuana and had to go back to cigarettes in order to stop smoking marijuana.

The patient's medical history is significant for a cyst removed from her breast, a diagnosis of Mitral Valve Prolapse and some stomach problems which were diagnosed as a viral gastritis. The patient additionally has a history of 2 abortions which were uneventful. The patient's past psychiatric history is significant for being in therapy with a psychologist for several years due to marital problems. Nonetheless the patient has no demonstration of any major psychiatric syndrome and states that she has lots of neurotic problems.

The patient entered the program and selected a stop date with compliance and almost immediate emergence of severe symptoms of withdrawal. The patient states that she became incredibly irritable at work as well as experiencing significant anxiety, depression, difficulty concentrating and an extreme sick felling of a viral type syndrome. The patient states that she has experienced this in her previous attempts to stop smoking. This patient stopped for 4 days and became severely depressed, anxious, irritable with difficulty concentrating and was begun on 20 mg a day fluoxetine. She experienced an immediate sense of tranquilization and calming which permitted her to go home and go to bed for 12 hours. The next morning after a dosage of medication she felt dramatic relief from her urges, anxiety, difficulty concentrating, irritability, restlessness and impatience. The patient additionally states that she felt only mild cravings for cigarettes and her food carbohydrate cravings were substantially decreased. The patient complained of early side effects of nausea, headache and insomnia due to the medication. The patient was told that it was possible that her withdrawal syndrome is causing these side effects and the medication was continued at a dosage of 20 milligrams. She states that she dramatically improved on the medication with the ability to function despite these other symptoms of nausea and insomnia. Her overall clinical improvement was dramatic with a near total alleviation of the troublesome symptoms which she described in her other attempts to stop smoking.

EXAMPLE 7

Patient 7 is a 51 year old white male who has been smoking since the age of 9 years old. The patient has smoked 2 packs per day with 2 previous histories of trying to stop smoking by a cold turkey method. On both occasions when he stopped smoking he experienced severe symptoms of withdrawal. He was able to stop smoking for 3 years but experienced constant symptoms of urges and anxiety with difficulty concentrating, irritability, and restlessness related to his desire to smoke. The other occasion that he stopped smoking was for 3 months and he experienced the same symptoms that were described previously. The patient has smoked up to 3 packs per day for long periods of time but states his average has been 2 packs per day over the course of his life time.

The patient's past medical history is significant for the following. The patient has back pain which was diagnosed as the Herniated Disc for which he had a laminectomy and treatment with Prednisone. The patient was addicted to Prednisone for 3 months and had to be tapered slowly with symptoms of pain and emotionally liability during this period. This was successfully completed and Prednisone has not been used for several years. The patient additionally suffers from extremely high cholesterol and triglyceride levels and marginal high blood pressure. The patient's father died of cancer of the lungs and smoked cigars and cigarettes heavily and his mother suffers from Diabetes.

The patient had a divorce over a year ago which precipitated an acute crisis in which he entered into therapy for counselling and emotional support. He has functioned extremely well throughout his life with perseverance and ability to accomplish goals and states that his inability to stop smoking has been a major failure in this life. He has done extremely well on the medication and has participated in the program very actively for stopping smoking.

This patient has been able to pick a stop date which he successfully completed and stopped for several days with significant symptoms of depression, anxiety, irritability and severe urges for cigarettes. The patient was begun on 20 milligrams a day of fluoxetine with a notable significant decrease in his urges and carbohydrate cravings as well as his irritability within 12 hours. The patient experienced no other side effects to the medication.

EXAMPLE 8

Patient 8 is a 30 year old white female who has a history of smoking 2 packs per day for the last ten years. She began smoking at age 20 and has tried to stop on different occasions with hypnotism and a computer tapering method called Life Sign. The patient maximally was able to stop for 4 days with severe urges, anxiety, depression, irritability, restlessness, and impatience occurring on both occasions. The patient states that she was unable to stop smoking due to these withdrawal symptoms and fears there reoccurrence on this program.

The patient's past psychiatric history is significant for a heroin addiction treated in an inpatient rehab with no subsequent reoccurrence of her addiction. The patient has been totally sober for 6 years and is free of major psychiatric symptomatology. The patient states that her symptoms of withdrawal from nicotine are as severe as those she experienced while coming off of heroin. She described that they are both physical and psychological symptoms which are extremely debilitating to her and feel much worse than heroin withdrawal.

The patient's medical history is significant for a history of an accident in 1980 when she smashed her right leg as well as a history of convulsion which was probably related to her drug episodes. The patient additionally had Osteomyelitis due to an infection from the accident when she broke her leg.

The patient picked a stop date which she was able to complete and 3 days post withdrawal was experiencing severe urges, cravings for food, irritability, anxiety, depression and stated she would smoke if she wasn't able to control these symptoms. The patient was begun on 20 mg a day fluoxetine and within 3 hours felt dramatically improved on all spheres of symptoms. The patient stated that she no longer had cravings and her overall symptoms were within the tolerable range of normal. She continued on medication and has felt better than ever in her life in terms of being off of nicotine and not experiencing the symptoms which have gone alone with previous attempts to stop smoking. She states that the medication has been extremely beneficial to her and that these withdrawal symptoms would created urges for heroin which she had previously not experienced over the last several years.

It was clear that the withdrawal symptoms from cigarettes triggered heroin cravings as well as nicotine cravings on an intense basis. While on medication the patient experienced no urges for nicotine or heroin and states that she feels normal for the first time in several years because she is not smoking. This patient has a high sense of what it means to be sober and her model for addiction was well ingrained in terms of understanding that nicotine was in fact an addiction. She experienced significant relief to be free now of all drugs and states that the medication did not alter her sense of well being with regard to her sobriety. She demonstrated remarkable improvement on Prozac with a subsequent ability to control the severe urges through psychological and behavioral techniques.

EXAMPLE 9

Patient 9 is a 49 year old white male who started smoking from age 14 years old. The patient smokes on the average 4 packs per day which gives him a 140 pack-year history. The patient has attempted to stop smoking on 2 previous occasions. He has utilized nicotine gum and a behavioral approach program. The patient states that with nicotine gum he was smoking and chewing gum all at the same time with no particular decrease in his ability to stop smoking. He states that the gum made him extremely dizzy and nauseated and that he was unable to successfully complete that program. He additionally went to a behavioral program where he stopped smoking for 48 hours and experienced horrendous withdrawal which was categorized by severe depression, terrible irritability, and profound difficulty concentrating and coping on an emotional basis. The patient states that he went back to cigarettes and these symptoms completely disappeared.

The patient's past medical history is significant for hypercholesterolemia and borderline high blood pressure. His past psychiatric history is non significant. The patient has an alcohol problem which he states he utilized AA for and was able to recover for the last ten years ingesting no alcohol or other substances of abuse. The patient states he has continued to be extremely active in the fellowship and has become a leader in AA.

The patient's family history is significant for a father who died of a myocardial infarction at the age of 60 and smoked heavily. The patient's mother additionally smokes and has diabetes mellitus. The patient was interested in our program due to the fact that we have been able to attenuate the symptoms of withdrawal. The patient entered the program and was able to pick a stop date and utilized the behavioral preparation required for stopping cigarettes. The patient stopped cigarettes and within the first 24 hours went into a severe withdrawal syndrome. He stated that he would be unable to stop cigarettes and smoked in the first day and continued to smoke at a lesser level up to about 2 packs per day for the first week. The patient was asked to refrain from cigarettes for 24 hours and told that he would be placed on medication after blood draws and urine collections. The patient stopped and was placed on 20 mg a day fluoxetine and had a profound response in which he went home and went to sleep for 12 hours. The next morning he took his second dosage of medication and reported a highly significant response to medication with a complete decrease in his irritability, anxiety and symptoms of depression. The patient states that he had only mild to moderate urges for cigarettes with a significant improvement in his overall sense of well being. The patient experienced some drowsiness from the medication and his dosages were split to 10 mg twice a day to help with this problem. He improved consistently over the first week in terms of his response to the medication and was able to feel a complete abatement of urges for cigarettes as well as his sense of profound withdrawal.

EXAMPLE 10

Patient 10 is a 33 year old white male who has been smoking since age 12 years old on a level of about 2 packs per day. The patient has a 42 pack-year history and has never attempted to stop smoking. The patient describes that he fears stopping smoking due to nicotine withdrawal syndrome and the debilitation that he expects to experience from stopping.

The patient's past medical history is insignificant and his past psychiatric history is also insignificant. The patient has a history of having had an alcohol problem for which he attended AA for and has 4 years sobriety in the program of AA.

The patient's mother and father are both alive and the father was a heavy smoker with no apparent difficulties at present. The mother is in good health.

The patient entered the program and picked a stop date which he was able to accomplish. Post cessation he experienced moderate symptoms of withdrawal complaining of irritability, some depression, extreme sugar cravings and a sense of physical bloating. The patient states that he felt similar to when he gave up alcohol with a sense of physical illness accompanying the withdrawal syndrome. The patient was begun 5 days after cessation on 20 mg a day fluoxetine and experienced within 3 hours a sense of alleviation of all of the above symptoms. He states that the following morning he felt back to himself and had a significant response in terms of feeling in control of himself and alleviation of all the syndrome of withdrawal. The patient states that his cigarette cravings were minimal and controllable.

These patients are representatives of a pattern of response that has been consistently demonstrated with fluoxetine. The apparent response within 24 hours is an important factor since the acute sense of distress from withdrawal is something which needs to be eliminated immediately as opposed to waiting for several days for the medication to work. The patients, unilaterally, described a decrease in carbohydrate craving, appetite, normalization of anxiety and depression, a decrease in irritability and an overall return to a sense of well being. What has been made very clear from following these ten patients is that the acute syndrome of nicotine withdrawal and the severe cravings that emerge post cessation from smoking have been beautifully and effectively managed with fluoxetine. An aside is to note that several of the population are recovering substance abusers who have been unable to give up smoking as an addiction but successfully stopped other substances. This is a possible indication that nicotine is more highly addictive than these other substances.

As will be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

We claim:

1. A therapeutic method for treatment of nicotine withdrawal syndrome symptoms of a patient in need thereof which comprises administering to said patient a composition comprising a pharmaceutically acceptable carrier and fluoxetine in an amount between about 5 and about 40 milligrams per day so as to inhibit the reuptake of serotonin in the neurohumoral pathways of the central nervous system of said patient, so that physiological relief from said withdrawal symptoms is provided.

2. The method of claim 1, wherein said dosage is between about 10 and about 30 milligrams per day.

3. The method of claim 2, wherein said dosage is about 20 milligrams per day.

4. The method of claim 1, wherein said dosage is administered once a day.

5. The method of claim 1, wherein said dosage is administered twice a day at regular intervals.

6. The method of claim 1, wherein said dosage is administered three times a day at regular intervals.

7. The method of claim 1, wherein said pharmaceutically acceptable carrier is an additive or diluent selected from the group consisting of starches, sugars, gelatin, glycerine, water, polyvinyl alcohol and mixtures thereof.

8. The method of claim 1, further comprising administering said therapeutic composition between about 24 hours and about 48 hours after cessation of tobacco consumption.

9. The method of claim 1, wherein said amount administered is gradually reduced.

10. The method of claim 9, wherein said gradual reduction occurs over a period of approximately one year.

11. The method of claim 9, wherein said dosage is administered for at least six months prior to said dosage reduction.

12. The method of claim 1, wherein said therapeutic composition is administered between the hours of 6:00 a.m. and 9:00 a.m.

13. The method of claim 1, wherein said fluoxetine is administered in conjunction with one or more therapeutic agents effective in relieving one or more symptoms of nicotine withdrawal syndrome.

14. The method of claim 13, wherein said one or more therapeutic agents are selected from the group consisting of minor tranquilizers, major tranquilizers and other anti-depressants.

15. The method of claim 14, wherein said minor tranquilizer is a benzodiazepine.

16. The method of claim 14, wherein said anti-anxiety drug is selected from the group consisting of xanax and buspirone.

17. The method of claim 13, wherein said therapeutic composition further comprises said therapeutic agents.

18. The method of claim 13, wherein said therapeutic agents are administered separately.

19. The method of claim 1, wherein said therapeutic composition is administered orally in the form of tablets, capsules, dragees, granules or pills.

20. The method of claim 1, wherein said therapeutic composition is administered by injection or infusion.

* * * * *

UNITED STATES PATENT AND TRADEMARK OFFICE
CERTIFICATE OF CORRECTION

PATENT NO. : 4,940,585
DATED : July 10, 1990
INVENTOR(S) : Hapworth et al.

It is certified that error appears in the above-identified patent and that said Letters Patent is hereby corrected as shown below:

Column 1, line 6, "creating" should read --treating--.

Column 3, line 57, "eve" should read --even--.

Signed and Sealed this

Eighth Day of October, 1991

Attest:

HARRY F. MANBECK, JR.

*Attesting Officer*  *Commissioner of Patents and Trademarks*